US00PP16648P2

(12) United States Plant Patent
Bernuetz

(10) Patent No.: US PP16,648 P2
(45) Date of Patent: Jun. 13, 2006

(54) ***ARGYRANTHEMUM* PLANT NAMED 'OHMADSAVI'**

(50) Latin Name: *Argyranthemum×hybrida*
Varietal Denomination: OHMADSAVI

(75) Inventor: Andrew Bernuetz, Silverdale (AU)

(73) Assignee: Bonza Botanicals Pty., Ltd., Sydney (AU)

( * ) Notice: Subject to any disclaimer, the term of this patent is extended or adjusted under 35 U.S.C. 154(b) by 76 days.

(21) Appl. No.: 11/011,210

(22) Filed: Dec. 13, 2004

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
(74) *Attorney, Agent, or Firm*—Buchanan Ingersoll PC

(57) ABSTRACT

A new and distinct cultivar of *Argyranthemum* plant named 'OHMADSAVI' characterized by its semi-double inflorescence form with red/pink-colored ray florets and yellow/pink-colored disc florets, dark green-colored foliage, freely branching character, and upright, compact, and mounded growth habit.

1 Drawing Sheet

Latin name of the genus and species of plant claimed: *Argyranthemum×hybrida.*
Variety denomination: 'OHMADSAVI'.

BACKGROUND OF THE INVENTION

The present invention relates to a new and distinct cultivar of *Argyranthemum* plant botanically known as *Argyranthemum×hybrida* and hereinafter referred to by the cultivar name 'OHMADSAVI'.

The new *Argyranthemum* originated in a controlled breeding program in Winmalee, New South Wales, Australia during December 2001. The objective of the breeding program was the development of *Argyranthemum* cultivars that are freely branching, have a compact and upright growth habit, are freely flowering, and have unique flower coloration.

The new cultivar was developed via open pollination of numerous proprietary *Argyranthemum* varieties, not patented, in an isolated area. Seed was collected over an extended period from 2001 to 2002 and bulked, germinated and grown to maturity. One plant within the sowing was discovered and selected by the inventor on Sep. 24, 2002 in a controlled environment at Winmalee, New South Wales, Australia.

Asexual reproduction of the new cultivar by terminal stem cuttings since September 2002 at Winmalee, NSW, Australia and West Chicago, Ill. has demonstrated that the new cultivar reproduces true to type, with all the characteristics as herein described, firmly fixed and retained through successive generations of such asexual propagation.

SUMMARY OF THE INVENTION

The following characteristics of the new cultivar, having been repeatedly observed, and can be used to distinguish it as a new and distinct cultivar of *Argyranthemum* plant:

1. Semi-double inflorescence form with red/pink-colored ray florets and yellow/pink-colored disc florets.
2. Dark green-colored foliage.
3. Freely branching character.
4. Compact, upright, and mounded growth habit.

Plants of the new cultivar differ from plants of the possible parent cultivars primarily in flower color.

Plants of the new cultivar are similar to the cultivar OHAR01245, U.S. Plant patent application Ser. No. 10/741,695. However, in side-by-side comparisons, plants of the new cultivar differed from plants 'OHAR01245' in the following characteristics:

1. Plants of the new cultivar are taller than plants of 'OHAR01245'.
2. Plants of the new cultivar have larger inflorescences than plants of 'OHAR01245'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which more accurately describe the colors of 'OHMADSAVI'. The plants were grown in 10 cm pots for 13 weeks in a greenhouse at West Chicago, Ill.

DETAILED BOTANICAL DESCRIPTION

Figure 1:
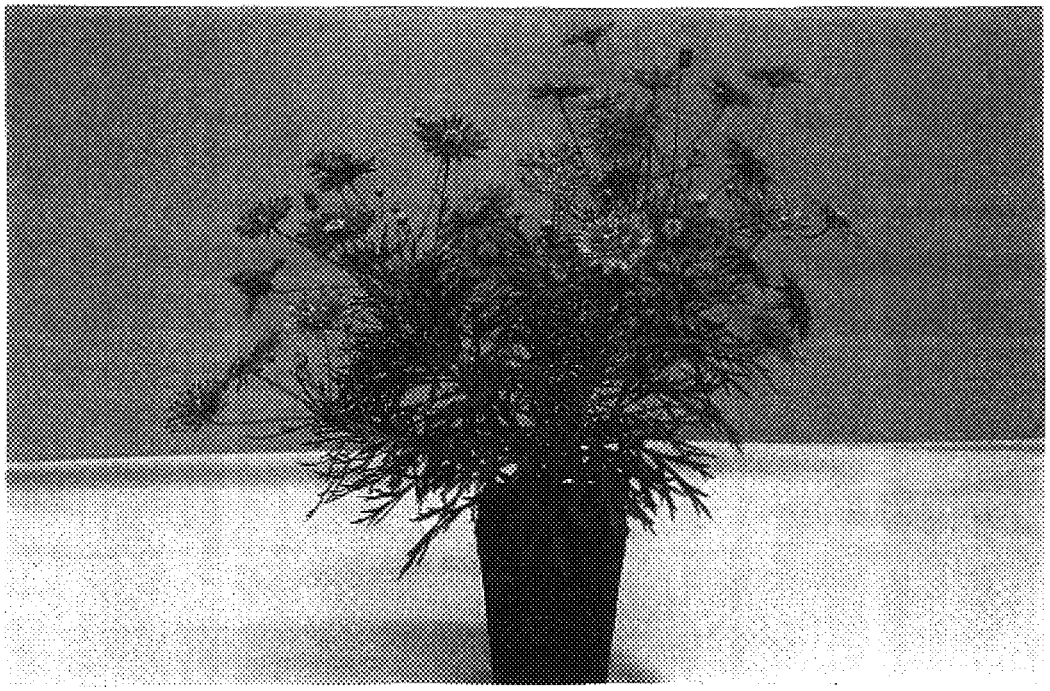
FIG. 1 illustrates a side view of the overall growth and flowering habit of 'OHMADSAVI' with one plant per pot.
Figure 2:
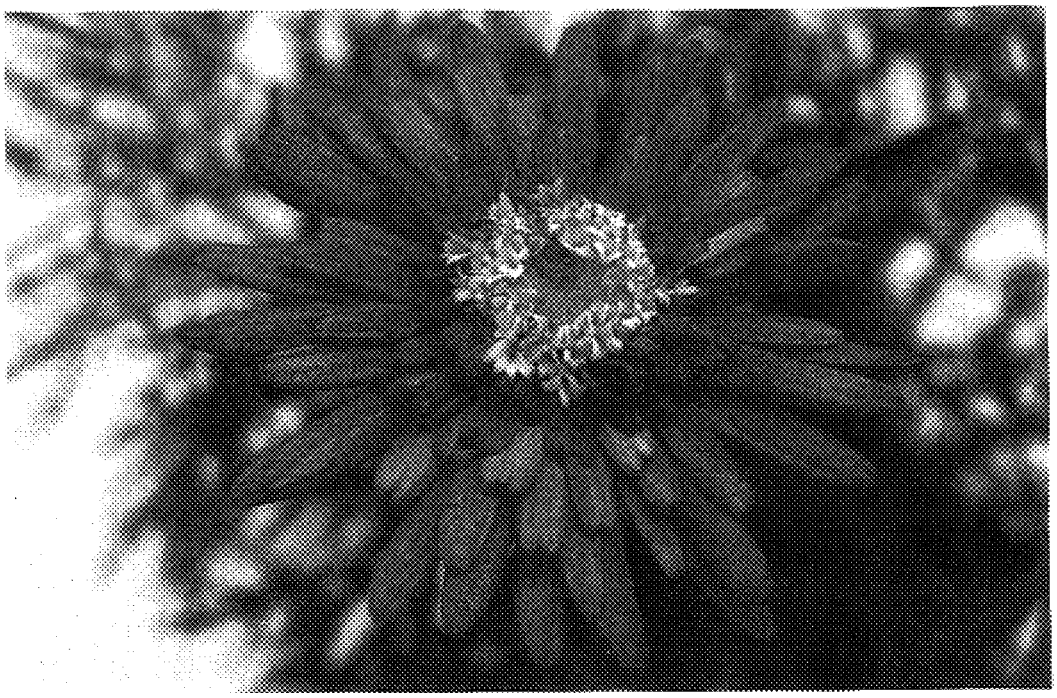
FIG. 2 illustrates a close-up view of an individual flower of 'OHMADSAVI'.

The new cultivar has not been observed under all possible environmental conditions to date. Accordingly, it is possible that the phenotype may vary somewhat with variations in the environment, such as temperature, light intensity, and day length without, however, any variance in genotype.

The R.H.S. Colour Chart of The Royal Horticultural Society, London, England, 2001 edition, was used in the identification of colors described herein, except where color terms of ordinary significance are used. The color values were determined on Oct. 9, 2004 between 10:00 and 11:00 a.m. under natural light conditions.

The following descriptions and measurements describe plants produced from cuttings taken from stock plants and grown in a double polycarbonate-covered greenhouse under conditions comparable to those used in commercial practice. The plants were grown at West Chicago, Ill. for 13 weeks in 10 cm pots utilizing a soil-less growth medium. Greenhouse temperatures were maintained at approximately 65°–78° F. (18°–25° C.) during the day and approximately 50°–60° F. (10°–15° C.) during the night. Greenhouse light levels were maintained at 6,000 to 9,000 footcandles during the day.

Botanical classification: *Argyranthemum×hybrida* cultivar OHMADSAVI.

Parentage: Open pollination of numerous proprietary *Argyranthemum* varieties, not patented.

Propagation:

*Type cutting.*—Terminal stem.

*Time to initiate roots.*—Approximately 6 to 8 days.

*Time to produce a rooted cutting.*—Approximately 21 to 28 days.

*Root description.*—Fibrous. Rooting habit — Freely branching.

Plant description:

*Crop time.*—Approximately 6 to 9 weeks in a 10 cm pot.

*Growth habit.*—Compact, freely branching. One or two pinches improves basal branching.

*Form.*—Upright, mounded.

*Size.*—Height: Approximately 31.5 cm from soil level to top of plant plane. Width (area of spread) — Approximately 42.1 cm.

*Lateral branch.*—Quantity per plant: Approximately 5. Strength: Strong. Length from soil level to base of peduncle: Approximately 17.4 cm. Diameter: Approximately 4.1 mm. Texture: Glabrous. Color: 146B. Internode length at middle of branch: Approximately 8.2 mm.

*Foliage.*—Quantity of leaves per branch: Approximately 24. Type: Simple. Fragrance: Slight. Arrangement: Alternate to whorled. Aspect: At an acute angle to the stem. Shape: Pinnatified. Margin: Deeply parted. Apex: Acute. Base: Attenuate, sessile. Venation pattern: Pinnate. Length: Approximately 7.1 cm. Width: Approximately 4.3 cm. Texture: Upper and lower surfaces are glabrous. Color of young and mature foliage: Upper surface: 146A with venation of 144C. Lower surface: 146B with venation of 144C.

Flowering description:

*Time to first flower.*—Approximately 8 weeks after planting of rooted cutting.

*Flowering habit.*—Freely flowering under outdoor growing conditions with substantially continuous blooming from spring through autumn and year round in greenhouse environment.

Inflorescence description:

*Appearance.*—Double composite form. Shape: Flat, round. Aspect: Facing upward or outward. Disc and ray florets develop acropetally on a capitulum. Fragrance: None.

*Quantity of flowers.*—Approximately 5 fully open flowers per main branch.

*Size.*—Diameter: Approximately 4 cm. Depth: Approximately 8.7 mm.

*Lastingness of inflorescence.*—Approximately 7–10 days.

*Bud.*—Rate of opening: Generally it takes 3–6 days for buds to progress from first color to fully open flowers. Shape: Spherical. Diameter: Approximately 6 mm. Depth: Approximately 6 mm. Color: Lighter than 70A.

*Ray florets.*—Quantity per inflorescence: Approximately 65, arranged in several overlapping whorls. Aspect: Cupped. Arrangement: Imbricate. Shape: Linear. Margin: Entire. Apex: Emarginate with three tips. Base: Attenuate and fused to form tube. Length: Approximately 1.8 cm. Width: Approximately 4.3 mm. Texture: Glabrous and ribbed. Color of young and mature ray florets: Upper surface: Closest to 71A. Lower surface: 70C. Tube texture: Sparsely glandular pubescent. Tube color: 145A.

*Disc.*—Diameter: Approximately 1.5 cm. Depth: Approximately 9 mm.

*Receptical.*—Shape: Cone. Diameter: Approximately 3 mm. Depth: Approximately: 2.3 mm. Color: 144B.

*Disc florets.*—Quantity per inflorescence: Approximately 104. Shape: Tubular with five lobes each having an acute apex and fused base. Margin: Entire. Length: Approximately 6.3 mm. Diameter at apex: Approximately 2.1 mm. Diameter at base: Approximately 0.7 mm. Texture: Glabrous. Color of immature floret: 13A. Color of mature floret: 9A with the oldest florets having tips of 71A. Calyx: Shape: Tubular. Length: Approximately 2 mm. Diameter: Approximately 1 mm. Texture: Glabrous. Color: Colorless, translucent.

*Phyllaries.*—Quantity per inflorescence: Approximately 22. Arrangement: Imbricate, arranged in several rows. Shape: Lanceolate. Margin: Entire. Apex: Acute. Base: Truncate. Length: Approximately 4 mm. Width: Approximately 2 mm. Texture: Glabrous, papery along edges. Color of upper and lower surface: Closest to 144A.

*Peduncle.*—Strength: Strong. Aspect: Erect. Length: Approximately 8.8 mm. Diameter: Approximately 1.1 mm. Texture: Puberulent. Color: 145A.

*Reproductive organs.*—Androecium: Present on disc florets only. Stamens: 5, fused around style. Anther shape: Linear. Anther length: Approximately 1.5 mm. Anther color: 5C. Amount of pollen: Moderate. Pollen color: 13A. Gynoecium: Present on ray and disc florets. There is one pistil per floret. Pistil length: 4 mm. Stigma shape: Two parted. Stigma length: 1 mm. Stigma color: 150C. Style length: Approximately 2.5 mm. Style color: 144C. Ovary diameter: Approximately 0.5 mm. Ovary color: 144C.

Seed and fruit production: Neither seed nor fruit production has been observed.

Disease and pest resistance: Resistance to pathogens and pests common to *Argyranthemum* has not been observed.

What is claimed is:

1. A new and distinct cultivar of *Argyranthemum* plant named 'OHMADSAVI', substantially as herein shown and described.

* * * * *